United States Patent [19]

Pilliar et al.

[11] Patent Number: 5,344,457
[45] Date of Patent: Sep. 6, 1994

[54] POROUS SURFACED IMPLANT

[75] Inventors: Robert M. Pilliar; Douglas A. Deporter, both of Toronto; Phillip A. Watson, Don Mills, all of Canada

[73] Assignee: The University of Toronto Innovations Foundation, Ontario, Canada

[21] Appl. No.: 12,626

[22] Filed: Feb. 2, 1993

Related U.S. Application Data

[63] Continuation of Ser. No. 649,700, Feb. 1, 1991, abandoned, which is a continuation-in-part of Ser. No. 517,517, Apr. 26, 1990, abandoned, which is a continuation of Ser. No. 420,689, Oct. 11, 1989, abandoned, which is a continuation of Ser. No. 138,340, Dec. 28, 1987, abandoned, which is a continuation-in-part of Ser. No. 864,805, May 19, 1986, abandoned.

[51] Int. Cl.$^5$ ............... A61F 2/28; A61C 8/00; A61C 13/10
[52] U.S. Cl. ............... 623/16; 433/174; 433/175; 433/191; 433/193; 433/195
[58] Field of Search ............... 433/172, 173, 174–176, 433/191–194; 623/16

[56] References Cited

U.S. PATENT DOCUMENTS

| | | | |
|---|---|---|---|
| 943,113 | 12/1909 | Greenfield | 433/173 |
| 2,857,670 | 10/1958 | Kiernan, Jr. | 433/173 |
| 3,855,638 | 12/1974 | Pilliar | 3/1 |
| 4,164,794 | 8/1979 | Spector et al. | 3/1.912 |
| 4,223,413 | 9/1980 | Aoyagi et al. | 3/1.9 |
| 4,259,072 | 3/1981 | Hirabayashi et al. | 433/173 |
| 4,366,183 | 12/1982 | Ghommidh et al. | 427/2 |
| 4,631,031 | 12/1986 | Richter | 433/173 |
| 4,705,694 | 11/1987 | Buttozzoni et al. | 427/2 |
| 4,758,161 | 7/1988 | Niznick | 433/173 |

FOREIGN PATENT DOCUMENTS 0151951  8/1984  Japan .

OTHER PUBLICATIONS

R. Adell et al., *A 15-Year Study of Osseointegrated Implants in the Treatment of the Edentalous Jaw;* Int. J. Oral. Surg. 1981: 10:387–416.

Hench et al., *Adhesion to Bone*, Biocompatability of Orthopedic Implants, pp. 129–170.

Lange et al., *Permucosal Oral Implants: the Relationship Between Sealing and Fixation, Tissue Intergration in Oral and Maxillo-Facial Reconstruction,* pp. 278–283 Proceedings of an Intenational Congress, May 1985, Brussels, (Excerpta Medica 1986).

Young et al., *Porous Titanium Endosseous Dental Implants in Rhesis Monkeys: Micro-Diography and Histological Evaluation,* J. Bromedical Materials Research, vol. 13, pp. 843–855 (1979).

Niznick, *The Corp. Vent Impalnt System,* Implantology, Nov. 1983, vol. 73, No. 11, pp. 13–15.

Primary Examiner—David Isabella
Assistant Examiner—Debra S. Brittingham
Attorney, Agent, or Firm—Wyatt, Gerber, Burke and Badie

[57] ABSTRACT

There is disclosed an implant for anchoring in bone and/or fibrous connective tissue and to which a prosthesis such as a dental bridge may be connected through connecting components. The implant is of tapered design defining a wide top portion for connection to the connecting components and a tapered body comprising upper and lower regions. The lower bone-engaging region of the implant is provided with a porous surface into which bone may grow thereby anchoring the implant. The upper region of the implant has a surface suitable for bone attachment which is different from the surface of the lower region. In one embodiment, the upper portion has a larger taper angle than the rest of the implant for increased stability and stress transfer to the surrounding bone. In another embodiment, the surface of the upper region is coated with a bioreactive coating to allow direct bonding of bone and/or soft connective tissue (gingival tissue) thereby inhibiting epithelial migration apically.

20 Claims, 4 Drawing Sheets

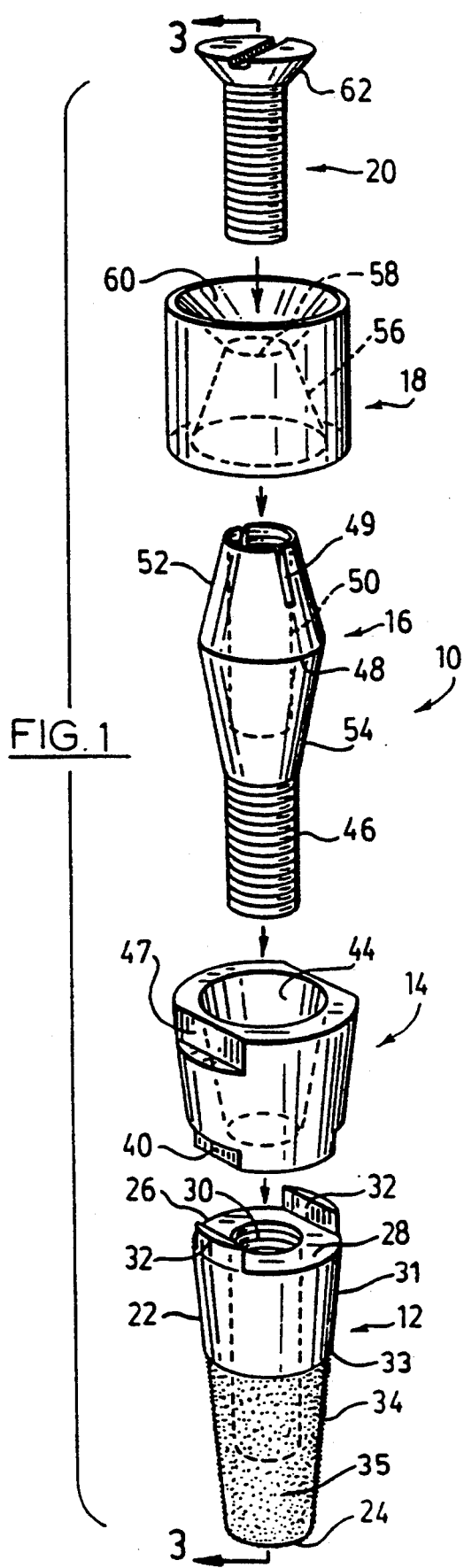
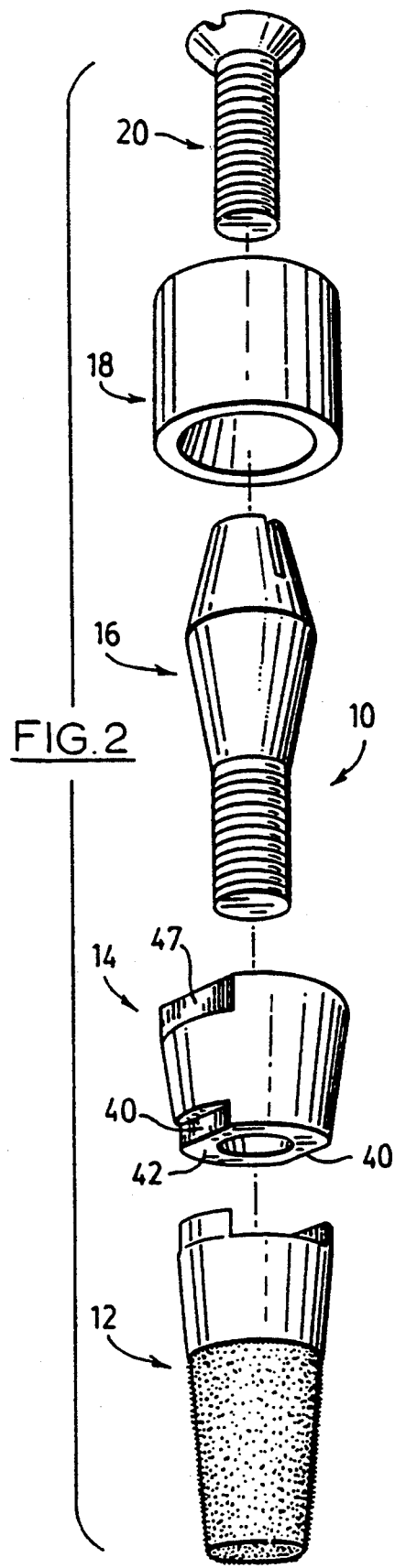

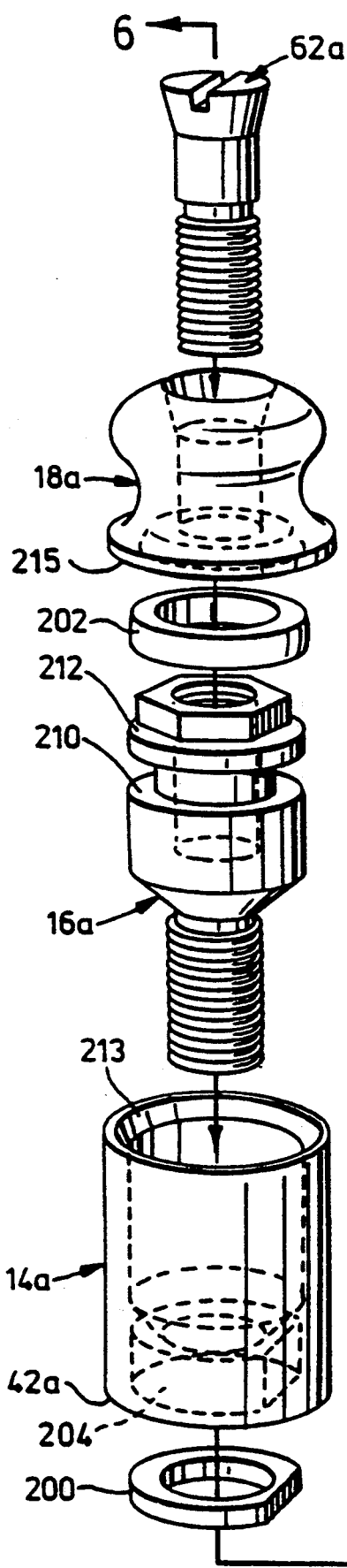
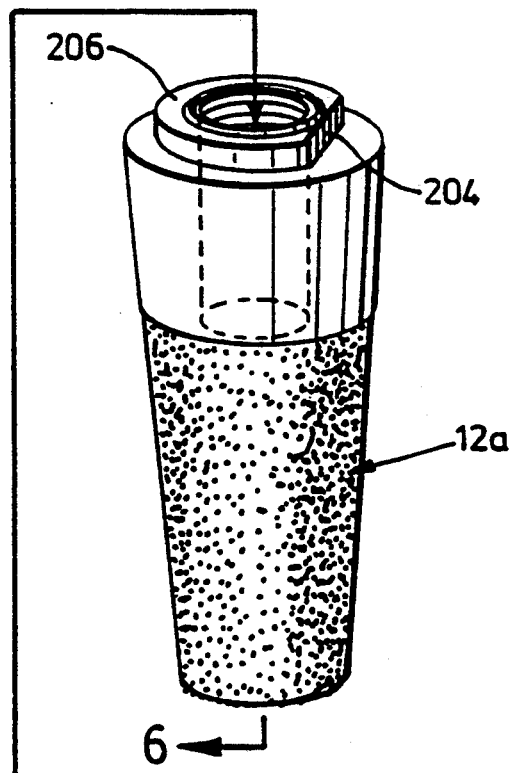
FIG. 5
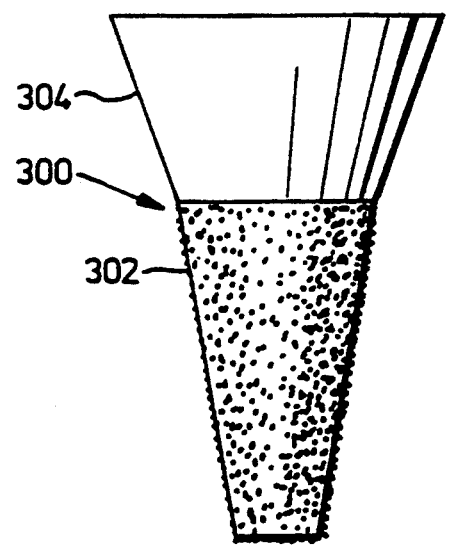
FIG. 7

POROUS SURFACED IMPLANT

This application is a continuation application of application Ser. No. 07/649,700, filed Feb. 1, 1991, now abandoned, which is a continuation-in-part of application Ser. No. 07/517,517, filed Apr. 26, 1990, now abandoned, which is a continuation of application Ser. No. 07/420,689, filed Oct. 11, 1989, now abandoned, which is a continuation of application Ser. No. 07/138,340, filed Dec. 28, 1987, now abandoned, which is a continuation-in-part of application Ser. No. 06/864,805, filed May 19, 1986, now abandoned.

FIELD OF THE INVENTION

The present invention relates to prosthesis and, more particularly, to means for connecting prostheses to bone.

BACKGROUND OF THE INVENTION

Devices of the type described herein serve generally to couple mechanically percutaneous prosthetic members for attachment of artificial eyes, ears, limbs, and, in particular, teeth to bone. Typically, such devices comprise two connectable main components; an implant component for integration with bone which serves an anchoring function and a separate support component that traverses epithelial tissue to which the prosthesis may be attached and subsequently coupled to the implant.

The tenacity with which the bone is able to retain the implant in situ is one factor which determines the success of devices of this type. This factor depends on the stability of the implant relative to the bone during the early healing phase following implant insertion and on the transfer of a small amount of stress from the implant to the bone in order to maintain bone and to increase bone density and strength.

Prior art proposals focus largely therefore on the means by which the implant is anchored within the bone.

One such proposal relating specifically to dental prostheses is disclosed in *Int. J. Oral Surg.* 1981; 10; 387–416, Adell et at. In that arrangement, screw-threaded cylindrical implants are provided upon which a dental bridge may be connected through a plurality of connectable supporting elements. Cooperation between the implant and the bone is provided by a bore in the jaw which is tapped to provide screw-threading complementary to the implant. A similar arrangement is proposed by Niznick in *Implantology*, November, 1983 Volume 73, Number 11, pages 13–15 in which the threaded cylindrical implant is provided near its base with channels through which bone is permitted to grow in order to enhance co-operation between the bone and the implant.

Another means by which an implant may be anchored in position is taught by Pilliar in U.S. Pat. No. 3,855,638. This reference describes a surgical prosthetic device with a porous metal coating. The dental implant taught by Pilliar comprises a cylindrical red having a porous coating on at least the areas of the implant in contact with and adjacent to bone. Such a porous coating allows for tissue ingrowth and tissue ossification. This reference suggests that the implant may also have a porous coating on the entire surface of the implant to encourage soft tissue growth in regions contacting such soft tissue. The provision of a porous coating on the entire implant surface provides, it is stated, a very rigid structure.

Further, in U.S. Pat. No. 4,223,412, Aoyagi et al. teach an implant having dental application comprising a pair of arms which extend into the receiving implant cavity. The entire surface of the implant is coated with a mixture of ceramics and hydroxyapatite, a mixture which has been shown to have excellent compatibility with living tissues. Such a coating has affinity to living tissue which allows for fixation of the implant.

Tapered implant devices are known. Greenfield (U.S. Pat. No. 943,113) provides a tapered implant frame for an artificial tooth. This design comprises a ribbed frame to allow for bone growth around and throughout the frame in order to secure the implant in position. Kiernan et al. (U.S. Pat. No. 2,857,670) also disclose a tapered implant for dental application. The way in which this implant is anchored in position, however, is by means of a plurality of serrations to allow bone growth throughout the implant. Outwardly extending studs are also provided on the implant for the purpose of gripping the surrounding bone structure.

Spector et al., in U.S. Pat. No. 4,164,794, disclose prosthetic devices having dental application. Specifically, there is disclosed a device having a tapered body, the entire surface of which is coated with a porous coating. However, it has recently been shown by Deporter et al. (J. Dent. Res. 67, 1190–1195, 1988) that the risk of infection from dental plaque may be increased when the entire length of the root component of such an implant is porous-coated. This risk is particularly increased when regions of the porous coating become directly exposed to the oral cavity.

It would be desirable to have an implant which, in use, possesses optimum fixation between the implant and the bone together with a reduced probability of the occurrence of infection.

SUMMARY OF THE INVENTION

It is an object of the present invention to provide a novel implant useful to connect prostheses to bone and which mitigates at least one of the disadvantages of prior implants.

Thus, according to one aspect of the present invention, there is provided an implant for insertion into bone through an epithelial and fibrous connective tissue layer adapted for connection of a prosthesis thereto, comprising:
- a top portion for supporting a mechanical component to which a prosthesis may be connected; and
- a body comprising an upper bone-attachment region tapering to a lower bone-engagement region having a porous surface,
- wherein the upper bone-attachment region comprises a substantially non-porous surface and is capable of enhancing bone attachment thereto.

According to another aspect of the present invention, there is provided a device for connecting prosthesis to bone comprising:
- an implant having a top portion for supporting a mechanical component to which a prosthesis may be connected, and a body comprising an upper bone-attachment region tapering to a lower bone-engagement region having a porous surface, the upper bone-attachment region comprising a substantially non-porous surface and being capable of enhancing bone attachment thereto; and a mechanical component for connection to a prosthesis, the mechanical component comprising a collar, connecting means for connecting the collar to the implant, a coping for integration with the prosthesis, and retaining means for connecting the coping to the connecting means.

The combination in an implant of a tapered body having two surfaces, specifically a lower or apical porous surface for primary fixation of the implant (bone-engagement) and an upper or coronal surface which promotes the maintenance of bone surrounding this surface of the implant (bone-attachment), provides unexpected and surprising advantages over implants described in the prior art.

The tapered shape of the body of the implant is beneficial, particularly in the case of dental implants, since it provides a self-seating structure. Specifically, many implants, such as dental implants, are exposed to constant or regular compressive forces. The conical shape of the present implant minimizes apical movement of the implant providing stability which encourages bone ingrowth in the lower bone-engagement region of the implant body.

A porous coating on the surface of the lower bone-engagement region of the implant body provides for primary fixation of the implant to the bone as it allows for bone ingrowth to the porous coating. The porous coating has been found to provide a desirable degree of engagement between implant and bone without the need for threading of the bone which requires specialized skills and equipment.

It has also been found that the fixating property of such a porous coating is most effective if early movement of the implant is minimized or prevented. In the present case, such early movement is minimized or prevented by the tapered geometry of the body of the implant. Thus, the implant of the present invention provides means by which more secure anchorage of the implant within a receiving cavity is achieved.

The porous surface on the lower bone-engagement region of the implant body may be in the form of a coating comprised of discrete particles adhered to the implant surface into which bone may grow thereby fixing the implant and providing long term stability. Preferably, the porous surface comprises a porosity of from about 10 microns to about 800 microns. More preferably, the porosity of the porous surface is from about 50 to about 400 microns. Porosity ranges stated herein are defined by pore size.

In a preferred aspect of the present invention, interstitial bone growth may be enhanced by application of a protein coating over the porous surface of the lower bone-engagement region of the implant body. Such a protein coating may comprise a protein such as collagen.

The upper bone-attachment region of the implant body comprises a substantially non-porous surface. Thus, the surface of this upper region of the implant body is relatively smooth in comparison to the porous surface of the lower bone-engagement region. Preferably, the surface of the upper region is such that it has a porosity of not more than about 5 microns root mean square average (a surface with a porosity of about 5 microns root mean square average has the texture of a slightly roughened surface). It will be appreciated that a substantially smooth surface is included within this definition.

Preferably, the upper bone-attachment region of the implant body has a surface coated with a bioreactive material. The exact nature of the bioreactive material is not particularly restricted and may be a hydroxyapatite such as calcium hydroxyapatite. Such a coating is advantageous in that it provides an osteoconductive surface which promotes bone formation, attachment and retention as high as possible on the implant. Another feature of such a bioreactive coating is the provision of a smooth surface which is effective in preventing entrapment of bacteria. Specifically, it has been surprisingly and unexpectedly discovered that such a surface encourages bone formation and retention as high as possible on the implant body resulting in attachment of the bone to the upper surface. This provides secondary fixation of the implant within the bone cavity and minimizes the depth of gingival pockets which may form around the implant.

While not wishing to be bound by a specific scientific theory or mode of action, it is believed that bone growth is stimulated by a constant small amount of stress acting on the bone by a "foreign" object. In the absence of such stress, the bone may resorb which can cause formation of gingival pockets increasing the risk of infection. It is believed that the combination of a tapered implant body with the upper bone-attachment region discussed above assists in mitigating the occurrence of gingival pocket formation. The tapered shape provides effective transfer of stress to surrounding bone during occlusal function in comparison to the stress provided by a cylindrical implant. This may be due to the fact that application of a vertical force on a tapered implant results in two force components acting on bone surrounding the implant, specifically a normal force component and a shear force component. Effective transfer of stress enhances bone density and formation in the region of the implant. The provision of the upper bone-attachment surface discussed above provides the creation of a seal between the implant and the bone which serves to prevent substantially the development of gingival tissue invagination and the subsequent occurrence of implant failure or bacterial infection leading to various forms of gum disease.

BRIEF DESCRIPTION OF THE DRAWINGS

A preferred embodiment of the invention, particularly in respect of its application with dental prostheses, is hereinafter described by way of example only with reference to the accompanying drawings in which:

FIG. 1 is a perspective exploded view of a dental implant device showing individual components as viewed at an angle from above;

FIG. 2 is another exploded view of the same device shown in FIG. 1 at an angle from below;

FIG. 5 is an exploded perspective view of another dental implant from above;

FIG. 7 is a side view of an alternative implant.

DETAILED DESCRIPTION OF A PREFERRED EMBODIMENT

Figure 3:
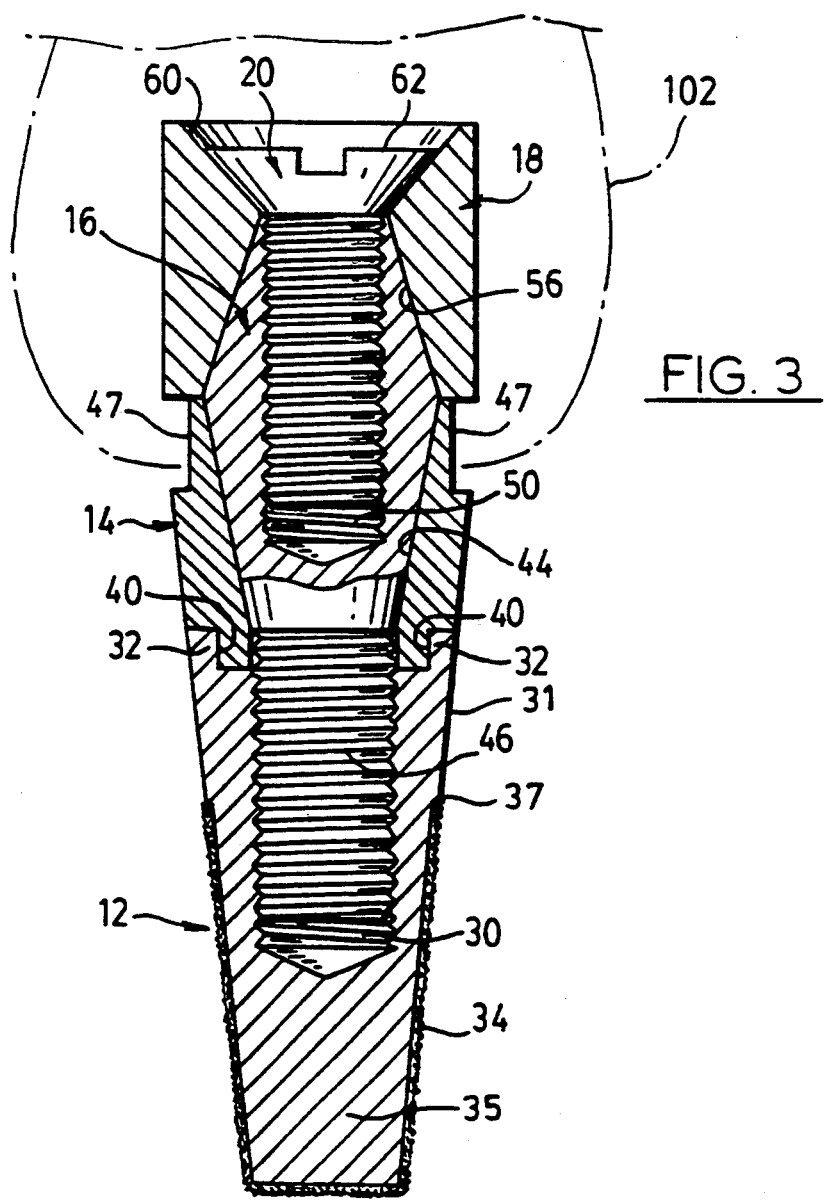
FIG. 3 is a sectional view along line 3—3 of FIG. 1 with parts in assembled condition.

Referring now to FIGS. 1 and 2, there is illustrated a device 10 comprised of an implant 12, a collar 14, a connecting screw 16, a coping 18 and a retaining screw 20 all of which are preferably formed from a titanium alloy including aluminum and vanadium. Pure titanium and other biocompatible materials known in the art may also be used.

Implant 12, which is to be integrated with bone, has a tapered body 22 of frusto-conical shape delimited by a base 24 and a top 26. Top 26 of the implant 12 defines a planar surface 28 from which a screw-threaded bore 30 extends vertically into but not through the tapered body 22. The planar surface 28 is bordered by a pair of projections 32, diametrically opposed, which serve as interlocking elements for engagement with complementary formations on the undersurface of the collar 14.

Implant 12 comprises an upper bone-attachment region 33 having an outer surface 31 which is substantially non-porous. This smooth upper portion extends over about 2 mm of the uppermost length of the implant.

Figure 4:
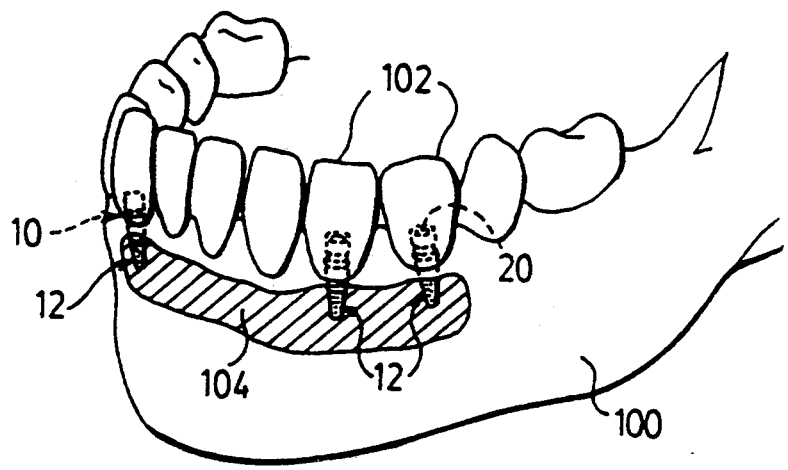
FIG. 4 is a perspective view of a series of devices in position on the jaw and supporting a dental bridge.

Implant 12 also comprises a lower bone-engagement region 35, including the base 24, provided with a porous surface 34 comprised of a network of discrete particles. The porous surface 34 provides interstices into which bone is permitted to grow once implant 12 is accommodated within the bone (FIG. 4). The discrete particles of porous surface 34 are preferably formed from the same titanium alloy from which implant 12 is formed, although other non-biodegradable, non-toxic, tissue-compatible materials may be used which admit of adherence to the material from which the implant is formed. Examples of such other materials include cobalt-chromium beads, hydroxyapatite, aluminum oxide and ceramic materials known in the art.

In a particularly preferred method of applying the porous coating, the desired material is powdered to provide spherical or irregularly shaped particles which are then admixed with adhesive and applied as a composition to the implant. The implant is then subjected to high temperature sintering, under vacuum, by which the adhesive is removed and the particles fused to the surface and to one another to form an interstitial matrix. The particles can vary from single layer to multilayer thickness. To accommodate the thickness of the particles deposited so that the surfaces of both upper bone-attachment region 33 and the lower bone-engagement region of the implant remain continuous, the porous coated region of the solid implant core is preferably stepped as shown in FIG. 3 at 37. By maintaining the porous coated region flush with the non-porous coated region of the implant, the sides of the implant will make intimate contact with the walls of the tapered bore in the jaw at the time of surgical placement.

The porous layer is provided to encourage growth of new bone into the interstices provided by the layer which growth provides for the anchoring function of the implant. Accordingly, the porosity of the layer is preferably controlled to within limits which, on one hand, allow influx of growing bone to a great extent and which, on the other hand, provide at least a minimum of surface to which the bone may anchor. It has been found that more preferred porosity ranges are on the order of from about 50 to about 400 microns although preferred porosities in the range of from about 10 to about 800 microns can be used. Successful results have been obtained using a porous layer derived from discrete particles of titanium-aluminum-vanadium having a porosity of from 50 to 400 microns for bone ingrowth and as low as 20 for connective tissue ingrowth. Also, the thickness of the porous layer may be varied provided preferably that the outer surface of the porous coating of the lower bone-engagement region remains flush with the upper bone-attachment region of the implant. Preferably, the thickness of the porous layer for materials made of titanium alloy is in the range of from about 20 to about 1,000 microns. The appropriate thickness of the porous layer deposited on a variety of other materials may vary depending upon the characteristic porosity of the deposited layer.

Collar 14 is adapted to be coupled to implant 12 in such a manner that rotation between the two components is precluded. This is accomplished by providing recesses 40 on the lower surface 42 of collar 14 which complement the projections 32 of implant 12. The collar defines a frusto-conically shaped bore 44 (FIG. 3) extending through its length allowing a screw-threaded shaft 46 of connecting screw 16 to be threadably engaged with a bore 30 of implant 12 so as to trap the collar 14 in position. Movement of the collar 14 in a vertical direction is restricted by an enlarged head 48 of the connecting screw and, particularly, by the nesting of a tapered lower portion 54 of the screw head within a complementary-shaped recess 44 of the collar 14, once screw shaft 46 is fully engaged within the implant 12. Since the torque applied to the connecting screw, when driving it into engagement with the collar 14, may be translated to the implant 12 if done forcefully, the collar 14 is provided with opposed parallel edges 47 for engagement with a suitable wrench. The torque applied while driving the connecting screw 16 can thus be countered by the wrench rather than by the implant 12, leaving the implant relatively undisturbed and anchored in the bone. To assist in driving of screw 16, the head of the screw is provided with a slot 49 for engagement by a suitable driver.

Head 48 of connecting screw 16 defines a screw-threaded bore 50 extending vertically into but not through connecting screw 16. An upper surface 52 of the connecting screw 16 is tapered so as to complement a correspondingly shaped recess 56 defined by coping 18. When properly aligned, a hole 58 in the top of a concave surface 60 of coping 18 aligns with screw-threaded bore 50 of connecting screw 16 so as threadably to engage a retaining screw 20 and trap coping 18 in position over the connecting screw 16. Concave upper surface 60 of coping 18 seats the head 62 of the retaining screw 20.

Advantageous features of the present invention may be realized in practice. In order to couple a dental prosthesis to bone, according to the preferred embodiment of the present invention, a bone 104 (FIG. 4) is drilled to define a bore of substantially the same contour as that of the implant. Thereafter, the implant is positioned in the bore, capped with a temporary cover (not shown) and left relatively undisturbed during a healing period. During the healing period, the bone surrounding the implant grows into the interstices in the porous layer of the lower bone-engaging region of the implant, thereby anchoring the implant in position and providing long term stability. Further, bone abuts against and attaches to the upper bone-attachment region of the implant.

After the healing period, the gingiva above the implant is opened, the temporary cap is removed and the collar, connecting screw, coping and retaining screw are accurately positioned on the implant. Thereafter, a cast is taken of the target region, i.e. the crestal region of the entire lower jaw 100 depicted in FIG. 4 including devices 10, and the cast is translated into a metal cast framework supporting acrylic or porcelain teeth 102. Copings 18 are detached from each implanted device and incorporated into the bridge at positions corresponding exactly to the positions of the implants 12. The teeth of the completed dental bridge are provided with holes, each of which align accurately with the coping holes and which in turn align the threaded bore defined by the connecting screw. To secure the dental bridge 102 in position, retaining screw 20 is threadably engaged with the connecting screw bore so as to trap the coping and the dental bridge, within which the coping has been integrated, into position.

A healing cap 62 is provided to be placed at the time of implant insertion. This element serves to prevent tissue growth within the threaded portion of the implant component 12.

A similar process is employed where only a single artificial tooth is to be coupled. In this case, the artificial tooth is fashioned specifically to envelop the coping to ensure that it is properly integrated. The porous surface of the lower bone-engagement region is particularly advantageous when used for a single tooth since it will resist torsional movement of the implant better than a screw threaded design.

Figure 6:
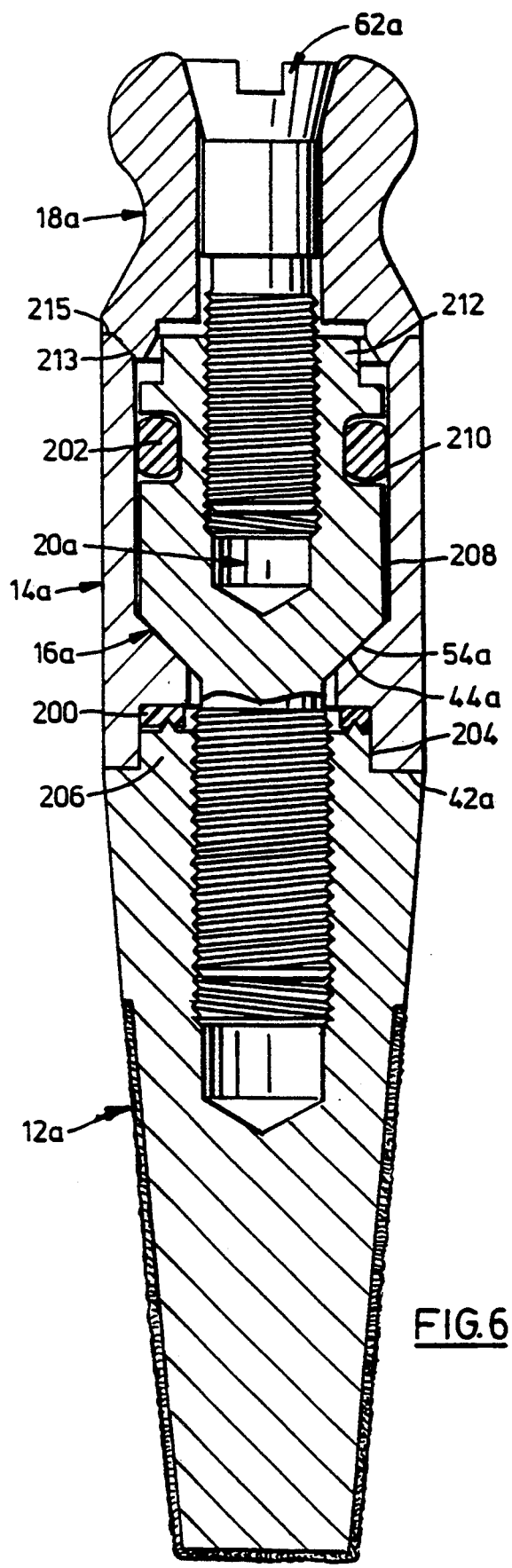
FIG. 6 is a sectional view along line 6—6 of the implant of FIG. 5.

Another embodiment of the invention is shown in FIGS. 5 and 6. Elements similar to those in FIGS. 1-4 have been given the same reference numeral followed by the suffix "A".

Generally, this embodiment is of similar construction to that of FIGS. 1-4, with a few exceptions. In this embodiment, seals 200, 202 are provided between implant 12A and collar 14A and between connecting screw 16A and collar 14A, respectively, to inhibit seepage of oral fluids into the device which may cause infection.

In addition, connecting screw 16A has a shorter tapered lower portion 54A to reduce the amount of friction between this portion and the complementary shaped recess 44A in collar 14A.

In the central portion 208 of collar 14A, connecting screw 16A is generally cylindrical and has an annular recess 210 for housing a seal 202. Above this recess is an upper hexagonal portion 212 provided for engagement by a wrench to apply torque to drive the connecting screw 16A.

At its lower surface 42A, the collar has a part-circular recess 204 which fits over a complementary-shaped protrusion 206 in implant 12A. The interconnection of recess 204 and protrusion 206 inhibits relative rotational movement of implant 12A and collar 14A.

The upper surface 213 of collar 14A and a lower surface 215 of coping 18A are each provided with mating tapered portions to inhibit relative movement therebetween.

FIG. 7 is an alternative embodiment of an implant 300. In this embodiment, the implant 300 has a tapered lower bone-engagement region 302 having a porous coating and a tapered upper bone-attachment region 304 having a substantially non-porous surface. The taper angle of region 304 is greater than that of region 302 to provide additional protection against bone resorption which may occur in the region of the upper portion and to encourage bone formation in this region. In this embodiment, the lower bone-engaging region 302 preferably has a taper angle of 5° (this angle can be up to 15°) and the upper bone-attachment region preferably has a taper angle of up to 30°.

By providing an implant having a tapered body, the present invention mitigates the disadvantages attendant with cylindrical implants known in the art. The tapered design of the implant provides for a stable initial friction fit between the bone and the implant. Subsequently, the close apposition of bone to porous coating and the transfer of stress to the apposed bone will encourage bone ingrowth and remodelling to effect sturdy attachment of implant to bone.

As a further desirable procedure of enhancing bone growth into the porous coating of the implant, the present invention contemplates use of a protein precoat over the porous layer of the lower bone-engagement region of the implant. It is believed that bone cells may be attracted by appropriate protein precoatings, allowing migration to occur more deeply and more rapidly into the interstices. Suitable protein precoats include collagen, fibronectin and platelet-derived growth factor on bone morphogenic protein. Precoating of the protein may be conducted using simple dipping techniques, generally known in the art. Hydroxyapatite or other calcium phosphate such as $\beta$-whitlockite may also be used as a precoating applied by plasma spraying, sputtering or other techniques generally known in the art.

Generally, the means by which a prosthesis may be attached to the implant may assume any number of configurations, subject to certain preferred criteria, so that the skilled artisan will appreciate that such implant may be adapted so as to couple to mechanical components other than that which is illustrated herein.

Important to the success of components for connecting a prosthesis to the implant, while not necessarily essential thereto, is the capacity of the connecting components to be detachable from the implant to allow the implant to be undisturbed during the healing period. Also, provision of a collar provides a means for connecting the coping, which is integrated with the prosthesis, to the implant which is integrated with the bone. To prevent rotation of the collar about the implant, a mechanical interlock should be provided at the interface of these two components and may also be provided between the collar/coping interface. Also, it is desirable to connect all of the components in such a manner as to prevent separation thereof in the vertical direction. Consideration also is given to the desirability of making the assembled fixture as streamlined as possible to prevent microbial flora from becoming established within pockets which might otherwise exist.

Moreover, it will be appreciated that the implant of the present invention is useful in anchoring prostheses other than dental prosthesis to bone. Such prostheses as eyes, ears and limbs may be coupled at the appropriate location using an implant of the type described herein together with the coupling components. Variation of specific design parameters may be required for example, where attachment to the comparatively thin cranium is required.

An embodiment of the present invention will now be exemplified by reference to the following non-limiting example.

PREPARATION OF THE IMPLANTS

Two different implant root designs fabricated from the titanium (Ti) alloy, Ti-6Al-4V (ASTMF 167), were used in this study.

The first design was identical to that previously reported (Deporter et al., *J. Dent. Res.*, 69, 1138–1145, 1990) except that the small vertical "step" previously used to mechanically interlock the implant and collar was replaced with an internal hexagonal receptacle designed to receive a corresponding male insert located on the apical aspect of the collar. The root component consisted of a truncated conical shape (taper angle=5°). The apical two-thirds of the root component (the lower bone-engagement region) of which had a porous-surface coating formed by sintering two to three layers of Ti-6Al-4V alloy particles (diameter 45 to 150 $\mu$m) on the Ti alloy implant substrate. The coronal one-third of the root component (the upper bone-attachment region) had a machined alloy surface with a surface finish less than 1.75 microns cla (center line average).

The second design differed only in that the coronal one-third was 3.465 mm in diameter (versus 3.500 mm for the non-hydroxyapatite-coated implants of the first design) and was roughened by sandblasting to give a 4.5 to 5.0 micron Ra (root mean square average) surface roughness (as measured with a Taylor-Hobson profilometer) in preparation for subsequent plasma spray coating with hydroxyapatite (HA). This roughened surface was ultrasonically cleaned and plasma dried (in air). The hydroxyapatite powder used had a particle size of less than 125 microns. The plasma spraying conditions used are summarized in Table 1. Plasma spray coating resulted in nominally the same overall diameter as the uncoated design (3.50 mm), although some variation resulted because of the irregularity of the plasma-sprayed layer.

TABLE 1
Plasma Spraying Conditions

| | |
|---|---|
| Equipment: | Metco MN |
| Particle Size Range: | 1-125 $\mu$m |
| Arc current: | 400 A |
| Arc voltage: | 60 V |
| Arc gas: | Nitrogen |
| Powder gas: | Nitrogen |
| Gun-Substrate distance: | 8 cm |
| Gun-Speed: | 10 cm/s |
| Powder flow rate: | 10-15 g/min. |
| Substrate Cooling: | By air |

The other components of the two implant systems were identical. As before all components of the implant systems were made by machining (Strite Industries, Cambridge, Ontario) while implant root components were porous-coated using methods previously described by Pilliar in *J. Biomed. Mater. Res.*, 21A, 1-33, 1987.

All implant components except the HA-coated root components were cleaned under sonication in the following sequential steps: (i) washing in 2% Decon (BDH chemicals) for 1 hour; (ii) three 3 minute washings in double-distilled, de-ionized water (DDDW); (iii) soaking in 28% nitric acid for 1 hour; and (iv) five 5 minute washings in DDDW. The cleaned implant components were then soaked for 1 hour in 100% ultrapure ethanol, air dried in a sterile air cabinet and autoclaved. In order to avoid possible dissolution of the hydroxyapatite coating, the HA-coated root components were washed only in DDDW three times successively for 15 minutes and were sterilized with dry heat for 40 minutes at 185° C.

FUNCTIONALITY OF THE IMPLANTS

Four male inbred beagle dogs (Laboratory Research Enterprises, Kalamazoo, Mich.) having initial weights of from 16 to 20 kg were used.

Implants were placed using a previously described (Deporter et al., *J. Dent. Res.*, 65:1064-1070, 1986) two-stage procedure in the regions of the mandibular third and fourth premolars which had been rendered edentulous six months prior to implantation. Two porous-coated implant root components without HA on the coronal third were placed on the left side and two porous-coated implant root components with HA coatings over this coronal region were placed on the right side of the mandible of each dog. After an initial healing period of six weeks, all root components were uncovered each to receive a collar and collar-retaining screw. Each pair of implants was then used to support a fixed bridge for an 18 month functional period during which the implants were cleaned thrice weekly using 0.2% chlorhexidine as previously described (Deporter et al., *J. Dent Res.*, 65:1071-1077, 1986).

During the functional period each implant was examined radiographically every four weeks with the dogs under general anaesthesia starting at the time of bridge insertion (approximately one week following placement of the collar and collar-retaining screw). A custom-made film holder was used, similar to one previously developed for use in humans (Cox and Pharoah, *J. Prosthet. Dent.*, 56:338-341, 1986), to achieve greater standardization of radiographic geometry in successive radiographs of the same implant. At each monthly examination, bridges were removed and the film holder was connected to each implant individually. Kodak ultra-speed DF-57 radiographic films (sizes #1 or #2), all from the same batch, were exposed using a Heliodent 70 (Siemens) x-ray machine with exposure factors of 70 KVp, 8 mA, 22 impulses and focal-film distance of 39.5 cm (15.5 inches). All films were developed manually using freshly mixed Kodak GBX developer and fixer (cat. 190 1859).

All radiographs were analyzed as follows. Films were transverse-illuminated and projected (magnification factor—6.6×) onto a monitor using a video camera (DAGE-MTI Inc., Michigan City, Ind., model N70). The images were digitized using a two image digitizing board (MATROX Corp., Dorval, Quebec) mounted in a graphics-oriented computer (Silicon Graphics Inc., Mountainview, Calif., model IRIS 3120) and a customized computer program was used to measure the crestal bone height adjacent to each of the mesial and distal surfaces of each implant. These height measurements were calculated and expressed by the computer as a fraction of the vertical height of the porous-coated segment of the root implant component. Since the crestal bone height was usually coronal to the machined surface-porous surface junction, the majority of height measurements are greater than 1.00.

ANALYSIS OF RESULTS

Following the 18 month functional period, the subjects were euthanized. Segments of mandible containing the implants were removed, processed and embedded in methylmethacrylate, and sectioned for histological assessment (Deporter et al., 1986; 1988). The sectioning technique was such as to provide two buccolingual, two mesial and two distal sections of each implant. In some cases it was possible to obtain three sections in one plane, while in others it was possible to obtain only one because of technical complications. The sections were examined both qualitatively and using computer-assisted morphometry. For the latter, black and white photomicrographs of each section at 26.5× magnification were prepared and analyzed using a digitizing tablet and Bioquant System IV software package (R & M Biometrics Inc., Nashville).

For each of the coronal one-third (machined only or HA-coated) and the apical porous-coated two-thirds of each aspect (buccal vs. lingual vs. mesial vs. distal) of each implant, the absolute length of implant surface in apparent direct contact with bone was determined as shown in Table 2. These data are referred to as the S-Contact (smooth coronal ⅓) and P-Contact (porous-coated apical ⅔), and are expressed as both the as-measured absolute lengths (S-Contact, P-Contact) and as a fraction (S-Contact Length Fraction—S-CLF, and the P-Contact length fraction—P-CLF) of the maximum length of the respective (i.e. coronal ⅓ or apical ⅔) implant surface available for contact with bone. The CLF fraction is equal to the length of bone in contact with the implant surface/length of available implant surface.

TABLES 2 (a) and (b)

A comparison of the mesial and distal aspects of the coronal one third or upper bone-attachment region (a) and apical two-thirds or lower bone-engagement region (b) of the two implant designs on the basis of bone height, absolute contact length and contact length fraction.

(a) coronal one third (upper region)

|  | S-Height (mm) | S-Contact (mm) | S-CLF (%) |
|---|---|---|---|
| non-coated | 0.77 | 0.61 | 30.12 |
| coated | 0.99 | 0.71 | 34.21 |
| coated minus | 0.23 | 0.10 | 4.09 |
| non-coated (±SE) | ±0.10 | ±0.10 | ±4.58 |

(b) apical two thirds (lower region)

|  | P-Height (mm) | P-Contact (mm) | P-CLF (%) |
|---|---|---|---|
| non-coated | 2.70 | 4.31 | 46.83 |
| coated* | 2.73 | 3.59 | 40.06 |
| coated minus | 0.04 | −0.72 | −6.77 |
| non-coated (±SE) | ±0.20 | ±0.36 | ±3.55 |

*corresponding coronal one-third coated with HA

In addition, the straight line vertical heights of bone in contact with each of the coronal ⅓ and apical ⅔ of each aspect of each implant were determined as shown in Table 3. These are respectively referred to as the S-Height (coronal ⅓) and the P-Height (for apical ⅔). These latter measurements were made directly from the histological slides using a stereomicroscope at 20× magnification and a Vernier gauge (Mitutoyo Canada, Streetsville, Ontario).

TABLES 3 (a) and (b)

These tables display the adjusted mean for bone heights, absolute contact lengths and contact length fractions for the coronal one third (a) and porous-coated apical two thirds (b) for each of the buccal and lingual aspects of the two implant designs.

(a) coronal one third

|  | S-Height (mm) | | S-Contact (mm) | | S-CLF (%) | |
|---|---|---|---|---|---|---|
|  | Buccal | Lingual | Buccal | Lingual | Buccal | Lingual |
| non-coated | 0.78 | 0.78 | 0.65 | 0.57 | 31.9 | 28.4 |
| coated | 1.03 | 0.99 | 0.72 | 0.71 | 34.5 | 34.4 |
| coated minus | 0.25 | 0.21 | 0.07 | 0.14 | 2.6 | 6.0 |
| non-coated (±SE) | ±0.13 | ±0.17 | ±0.14 | ±0.14 | ±6.4 | ±7.1 |

(b) apical two thirds

|  | P-Height (mm) | | P-Contact (mm) | | P-CLF (%) | |
|---|---|---|---|---|---|---|
|  | Buccal | Lingual | Buccal | Lingual | Buccal | Lingual |
| non-coated | 2.76 | 2.63 | 4.22 | 4.42 | 46.4 | 47.3 |
| coated* | 2.66 | 2.81 | 3.49 | 3.65 | 40.4 | 39.7 |
| coated minus | −0.11 | 0.17 | −0.73 | −0.76 | −6.0 | −7.6 |
| non-coated (±SE) | ±0.29 | ±0.32 | ±0.55 | ±0.53 | ±5.6 | ±5.2 |

*corresponding coronal one-third coated with HA.

Comparisons were made between the two implant designs controlling for variation among the dogs and possible positions, side and section of the implants, using analysis of variance. Computations were done using procedure GLM in the Statistical Analysis System to accommodate lack of balance (i.e. inequalities in the number of observations in all subcategories). Least square means were computed for observations made on the hydroxyapatite and control surfaces. These comparisons were carried out separately for the smooth and porous regions of each section of implant.

Finally, selected tissue-implant blocks that remained after sectioning for histological studies were completed, ground and polished using standard metallographic procedures in order to examine the HA coating after a prolonged in vivo exposure. For the specimen preparation, the final grinding and polishing directions were normal to the ceramic-metal interface with the grinding and polishing direction from the ceramic to the metal to avoid effects of metal smearing over the HA coating.

RESULTS

All of the implants became fixed by bone ingrowth and remained so throughout the 18 month functional period. The associated gingival tissues were in all cases keratinized and remained healthy in appearance.

The placement of a bioreactive hydroxyapatite plasma-sprayed coating over the smooth coronal region of the partially porous-coated dental implant results in bone retention to a greater height in this region. This is significant since loss of crestal bone adjacent to the non-coated implant generally results in periimplant pocket formation thereby increasing the susceptibility of an implant to plaque accumulation leading to tissue loss as well as infection.

What is claimed is:

1. An implant for insertion into bone through an epithelial and fibrous connective tissue layer and useful to connect a prosthesis thereto, the implant comprising:
   a top portion for supporting a mechanical component to which a prosthesis may be connected; and
   a body comprising an upper bone-attachment region tapering at an angle of about 5 degrees to a lower bone-engagement region formed from a material having a porous surface:
   wherein said upper bone-attachment region comprises a substantially non-porous surface capable of enhancing bone attachment thereto.

2. The implant defined in claim 1, wherein said non-porous surface of said upper bone-attachment region comprises a bioreactive coating.

3. The implant defined in claim 2, wherein said coating is calcium hydroxyapatite.

4. The implant defined in claim 2, wherein said non-porous surface is a roughened surface having a porosity of not more than about 5 microns root mean square average.

5. The implant defined in claim 4, wherein said nonporous surface is made of a titanium alloy.

6. The implant defined in claim 2, wherein said mechanical component is releasably retainable on said implant.

7. The implant defined in claim 2, wherein said upper bone-attachment region has a larger taper angle than said lower bone-engagement region.

8. The implant defined in claim 2, wherein said upper bone-attachment region is flush with said lower bone-engagement region.

9. The implant defined in claim 2, wherein the top portion of the implant defines engagement means for complementary engagement with said mechanical component to resist rotation of said mechanical component about said implant.

10. The implant defined in claim 2, wherein said porous surface has a porosity from about 50 to about 400 microns.

11. The implant defined in claim 1, wherein said porous surface has a porosity from about 10 to about 800 microns.

12. The implant defined in claim 1, wherein said porous surface is formed from discrete particles of the same material from which the implant is formed.

13. The implant defined in claim 1, wherein said porous surface is formed from a material selected from the group consisting of titanium alloy, cobalt-chromium, hydroxyapatite, aluminum oxide and ceramic material.

14. The implant defined in claim 13 wherein said protein is collagen.

15. The implant defined in claim 1, wherein protein is layered over said porous surface.

16. A device for connecting prosthesis to bone comprising:

an implant having a top portion for supporting a mechanical component to which a prosthesis may be connected, and a body comprising an upper bone-attachment region tapering at an angle of about 5 degrees to a lower bone-engagement region having a porous surface, the upper bone-attachment region comprising a substantially nonporous surface capable of enhancing bone attachment thereto; and a mechanical component for connection to a prosthesis, the mechanical component comprising a collar, connecting means for connecting the collar to the implant, a coping for integration with said prosthesis, and retaining means for connecting the coping to said connecting means.

17. The device defined in claim 16, wherein the upper bone-attachment region of said implant has a greater taper angle than that of the lower bone-engagement region of said implant.

18. The device defined in claim 16, wherein the upper bone-attachment region of said implant has a bioreactive coating thereon.

19. The device defined in claim 18, wherein said coating is calcium hydroxyapatite.

20. The device defined in claim 16, wherein the surface of the upper bone-attachment region of said implant has a porosity of not greater than about 5 microns root mean square average.

* * * * *